United States Patent

Nakagawa

[11] Patent Number: 5,537,859
[45] Date of Patent: Jul. 23, 1996

[54] METHOD OF DETERMINING THE AMOUNT OF THE FLUID CONTENT WITH A SMALLER SPECIFIC GRAVITY IN AIRTIGHTLY SEALED FLEXIBLE CONTAINERS ON A CONTINUOUS BASIS

[75] Inventor: Nobuhide Nakagawa, Chiba, Japan

[73] Assignee: House Foods Corporation, Osaka, Japan

[21] Appl. No.: 359,559

[22] Filed: Dec. 20, 1994

[30] Foreign Application Priority Data

| Dec. 21, 1993 | [JP] | Japan | 5-321864 |
| Dec. 21, 1993 | [JP] | Japan | 5-321865 |
| Dec. 27, 1993 | [JP] | Japan | 5-332218 |
| Dec. 27, 1993 | [JP] | Japan | 5-332219 |

[51] Int. Cl.$^6$ .............. G01J 5/00; G01N 33/28; G01M 3/36
[52] U.S. Cl. .............. 73/52; 73/32; 73/54.120; 73/61.440; 73/64.550; 73/32 R; 73/D5
[58] Field of Search .............. 73/52, 32 R, 447, 73/53.01, 54.12, 61.44, 54.42, 64.44, 64.55

[56] References Cited

U.S. PATENT DOCUMENTS

| 2,512,910 | 6/1950 | Bell | 73/15 |
| 3,678,276 | 7/1972 | Lampi et al. | 250/83.3 H |
| 3,812,270 | 5/1974 | Hartz | 426/231 |
| 3,814,248 | 6/1974 | Lawhead | 210/83 |
| 4,213,329 | 7/1980 | Raymond et al. | 73/52 |
| 4,327,574 | 5/1982 | Alberghini et al. | 73/19 |
| 4,672,840 | 6/1987 | Cullick | 73/38 |
| 4,907,443 | 3/1990 | Pailler | 73/52 |
| 4,924,695 | 5/1990 | Kolpak | 73/61.1 R |
| 5,309,750 | 5/1994 | Riley | 73/52 |
| 5,310,260 | 5/1994 | Schietinger et al. | 374/142 |
| 5,369,983 | 12/1994 | Grenfell | 73/40.7 |
| 5,377,126 | 12/1994 | Flik et al. | 364/557 |

FOREIGN PATENT DOCUMENTS

| 0206365 | 12/1986 | European Pat. Off. . |
| 1058646 | 3/1989 | Japan . |
| 1070334 | 3/1989 | Japan . |
| 6008921 | 1/1994 | Japan . |

*Primary Examiner*—Hezron E. Williams
*Assistant Examiner*—J. David Wiggins
*Attorney, Agent, or Firm*—Popham, Haik, Schnobrich & Kaufman

[57] ABSTRACT

A method determines the amount of the fluid content with a smaller specific gravity in an airtightly sealed flexible container containing contents with different specific gravities that are automatically separated from each other when held to a stationary state. The amount of said content is determined by externally applying pressure to the airtightly sealed flexible container to increase the inner pressure thereof and collecting data on the fluid content with the smaller specific gravity.

16 Claims, 4 Drawing Sheets

METHOD OF DETERMINING THE AMOUNT OF THE FLUID CONTENT WITH A SMALLER SPECIFIC GRAVITY IN AIRTIGHTLY SEALED FLEXIBLE CONTAINERS ON A CONTINUOUS BASIS

BACKGROUND OF THE INVENTION

Field of the Invention

This invention relates to a method of accurately determining on a continuous basis the amount of the fluid content with a smaller specific gravity in airtightly sealed flexible containers containing contents with different specific gravities that are automatically separated from each other when held to a stationary state such as liquid and gas or water and oil.

In the food industry, a cooked liquid food such as soup or stew contained in an airtightly sealed flexible container, or a retort pouch, with air or inert gas is subjected to an operation of so-called rotary retorting treatment for preservability, where the food is heated under high pressure while rotating the retort pouch.

The inventor of the present invention has found that the amount of gas content of each retort pouch significantly affects the sterilizing efficiency of the rotary retorting operation in terms of rate and extent of sterilization. The sterilizing effect of the rotary retorting treatment is particularly remarkable when the retort pouch contains gas by 2 to 50%. Additionally, the sterilizing effect on treated retort pouches is held to a highly uniform level and the degradation of the food content of the retort pouch by-overheating is minimized when the deviation in the gas content is confined between −3 and 10% among treated retort pouches.

On the other hand, if a retort pouch contains both liquid and gas and the viscosity of the liquid content is low, the liquid content is heavily affected by inertia to such an extent that the operation of determining the amount of the liquid content cannot be carried out immediately after the moved in container is held to a stationary state. The inventor of the present invention has found after a series of experiments that this problem is particularly remarkable when the coefficient of viscosity of the liquid content is lower than 5,000 CP.

Since a retort pouch made of flexible film is pliable and hence has a variable profile, it is very difficult to measure and regulate the amount of gas content or, more strictly speaking, the ratio of the gas content to the liquid content contained in it when compared with a rigid or quasi-rigid container such as a cup or a tray. No instruments are known to date that can quickly and accurately measure the gas content of retort pouches.

Additionally, as described above, if a retort pouch contains both liquid and gas and the viscosity of the liquid content is low, liquid content is heavily affected by inertia to such an extent that the operation of determining the amount of the liquid content cannot be carried out immediately after the moved in container is held to a stationary state. It has been discovered by the inventor of the present invention that this problem is particularly remarkable when the coefficient of viscosity of the liquid content is lower than 5,000 CP. Because of these and other problems, it has been believed to be difficult to measure on a continuous basis in a commercially feasible way the amount of the fluid content with a smaller specific gravity in airtightly sealed flexible containers containing contents with different specific gravities that are automatically separated from each other when held to a stationary state such as liquid and gas or water and oil.

Meanwhile, a measurement of the surface temperature distribution of an airtightly sealed container of the type under consideration shows that, if letters and/or decorative design segments are printed on the surface, the radiation of electromagnetic waves from the surface is differentiated between printed areas and plain areas so that no accurate measurement of surface temperature distribution can be achieved on such a container.

In view of the above identified technological problems, it is therefore an object of the present invention to provide a method of accurately measuring the amount of the fluid content with a smaller specific gravity in airtightly sealed flexible containers containing contents with different specific gravities that are automatically separated from each other when held to a stationary state such as liquid and gas or water and oil.

It is another object of the present invention to provide a method of accurately measuring on a continuous basis the amount of the fluid content with a smaller specific gravity in airtightly sealed flexible containers containing contents with different specific gravities that are automatically separated from each other when held to a stationary state such as liquid and gas or water and oil.

It is still another object of the present invention to provide a pressure plate to be used for accurately measuring on a continuous basis the amount of the fluid content with a smaller specific gravity in airtightly sealed flexible containers containing contents with different specific gravities that are automatically separated from each other when held to a stationary state such as liquid and gas or water and oil.

It is a further object of the present invention to provide a method of accurately measuring the surface temperature distribution of an object of examination including but not limited to an airtightly sealed container that carries printed letters and/or decorative design segments on the surface and irradiate electromagnetic waves therefrom.

SUMMARY OF THE INVENTION

According to a first aspect of the invention, the above objects are achieved by providing a method of determining the amount of the fluid content with a smaller specific gravity in an airtightly sealed flexible container containing contents with different specific gravities that are automatically separated from each other when held to a stationary state, wherein the amount of said content is determined by externally applying pressure to the airtightly sealed flexible container to increase the inner pressure thereof and collecting data on said fluid content with the smaller specific gravity.

The above first aspect of the present invention can be carried out in a number of different preferable modes as specifically described below. The amount of said content may be determined by externally applying pressure to part of the upper surface of the flexible container. In particular, external pressure may be applied by pressing a pressure plate having a hole against the container from above. Alternatively, the amount of said content may be determined by externally applying pressure to a lateral side of the flexible container. Still alternatively, the amount of said content may be determined by forming a projected image of said fluid content with the smaller specific gravity and calculating the volume of said content from the area of the projected image. The area of a projected image of said content with the smaller specific gravity may be determined by detecting the location of the outer boundary of the projected image. Alternatively, the area of the projected image of said content with the smaller specific gravity may be determined by processing a photographically taken image of said content. Still alternatively, the area of the projected image of said content with the smaller specific gravity may be determined by means of a fluoroscopic image of said content. Still alternatively, the area of the projected image of said content with the smaller specific gravity may be determined by means of an image of said content obtained by irradiating the container with infrared rays to produce temperature distribution data of the container and processing the obtained temperature distribution-data. The amount of said content may be determined by collecting data on the surface area of said content with the smaller specific gravity. Alternatively, the amount of said content may be determined by collecting data on the outer periphery of said content with the smaller specific gravity. The location of the outer boundary of a projected image of said content may be detected by means of at least a pair of light receiving devices. Alternatively, the location of the outer boundary of a projected image of said content may be detected by means of a linear sensor.

According to a second aspect of the invention, there is provided a method of determining the amount of the fluid content with a smaller specific gravity in an airtightly sealed flexible container containing contents with different specific gravities that are automatically separated from each other when held to a stationary state, wherein the amount of said content is determined by externally applying pressure to the airtightly sealed flexible container to increase the inner pressure thereof and collecting data on a projected image of the surface of said content with the smaller specific gravity in the airtightly sealed flexible container while intermittently moving the airtightly sealed flexible container with a maximum moving speed of not exceeding 0.1 m/sec.

According to a third aspect of the invention, there is provided a method of determining the amount of the fluid content with a smaller specific gravity in an airtightly sealed flexible container containing contents with different specific gravities that are automatically separated from each other when held to a stationary state, wherein the amount of said content is determined by externally applying pressure to the airtightly sealed flexible container to increase the inner pressure thereof and collecting data on a projected image of the surface of said content with the smaller specific gravity in the airtightly sealed flexible container while continuously moving the airtightly sealed flexible container with a maximum moving speed of not exceeding 0.1 m/sec.

The above third aspect of the present invention can be carried out in different preferable modes as specifically described below. The airtightly sealed flexible container may be moved horizontally, vertically or obliquely. Alternatively, the airtightly sealed flexible container may be moved along a horizontal circle.

According to a fourth aspect of the present invention, there is provided a pressure plate to be used for measuring the amount of the fluid content with a smaller specific gravity in airtightly sealed flexible containers containing contents with different specific gravities that are automatically separated from each other when held to a stationary state from a projected image of the surface of said airtightly sealed flexible container, wherein said pressure plate is provided with a central hole that satisfies the requirements of (1) b:a=1:1 to 2, where a is the length of the longest axis of the central hole of the pressure plate and b is the maximum possible length of the axis perpendicular to the longest axis of the central hole, (2) c:d=1:1 to 3, where c is the length of the longest axis of the central hole on the upper surface of the pressure plate and d is the length of the longest axis of the central hole on the lower surface of the pressure plate, and (3) t=0.05 to 1T, where T is the height of the flexible container and t is the thickness of the pressure plate.

Preferably, the pressure plate has a contour similar to that of the airtightly sealed flexible container. More specifically, if the airtightly sealed flexible container has a rectangular plan view, the pressure plate preferably has a rectangular plan view with dimensions substantially equal to those of the plane view of the container. The hole of the pressure plate is preferably circular or elliptic and has an area sufficiently large for measuring the amount the fluid content with the smaller specific gravity in the airtightly sealed flexible container.

While the pressure plate may be made of any material that can withstand the pressure applied thereto by the airtightly sealed flexible container, materials that can be used for the pressure plate include wood, bakelite, hard rubber, vinylchloride and teflon.

According to a fifth aspect of the present invention, there is provided a method of measuring the surface temperature distribution of an object of examination by means of electromagnetic waves irradiated from the surface, wherein the emissivity of electromagnetic wave of the surface is confined within a predetermined range by placing a sheet of translucent or opaque film in close contact with the surface of the object of examination.

A sheet of translucent or opaque film may be placed in close contact with the surface of the object of examination by simply placing the sheet of film on the surface of the object of examination or, alternatively, by bonding the sheet of film to a pressure plate having a central hole to cover the hole and pressing the sheet of film against the surface of the object of examination. The latter may be preferable when the object of examination is contained in an airtightly sealed flexible container.

While a sheet of film that can be used for the fifth aspect of the present invention may be made of any appropriate material so long as it is a sheet of translucent or opaque film, materials that can be used for such a sheet of film include silicon rubber, synthetic resins such as polyethylene and metal foil such as aluminum foil. For the purpose of the present invention, such a sheet of film preferably has a thickness of approximately 0.01 to 0.2 mm. When such a sheet of film is bonded to the pressure plate to cover the central hole, it is preferably made of a material that shows a certain extent of elasticity such as silicon rubber or synthetic resin Such as polyethylene.

According to the first aspect of the invention, by externally applying pressure to an airtightly sealed flexible container with a pressure plate, a portion of the container corresponding to the central hole of the pressure plate is caused to become relatively rigid and round and, if the central hole of the pressure plate is circular, the fluid content with the smaller specific gravity in that portion substantially shows the profile of a part of a sphere cut along a plane perpendicular to the axis running through the center of the circular central hole or along the lower surface of the pressure plate to provide data on a circular projected image of the fluid content with a smaller specific gravity. So, data on the content with the smaller specific gravity can be rapidly and accurately obtained to determine the amount of the content by collecting data on the circular projected image of the surface of said content with the smaller specific gravity.

According to the second and third aspects of the invention, by externally applying pressure to an airtightly sealed flexible container with a pressure plate, the content with the smaller specific gravity in the airtightly sealed flexible container can be caused to show a given profile, which can be maintained by moving the airtightly sealed flexible container with a maximum moving speed of not exceeding 0.1 m/sec. So, data on the projected image of the surface of said content with the smaller specific gravity can be collected accurately and, consequently, data on the content with the smaller specific gravity can be rapidly and accurately obtained from the data on the projected image of the surface of the content with the smaller specific gravity to determined the amount of the content.

Additionally, by externally applying pressure to an airtightly sealed flexible container with a pressure plate, the content with the smaller specific gravity in the airtightly sealed flexible container can be caused to maintain a given profile. As a result, data on the data on the content with the smaller specific gravity can be rapidly and accurately obtained from the data on the projected image of the surface of the content with the smaller specific gravity.

If the requirement (1) according to the fourth aspect of the present invention is not met for a pressure plate to be used for an airtightly sealed flexible container, the container is subjected to intolerable force, which causes the container to wrinkle, when the container is pressed with the pressure plate. Then, the area or the projected image of the content with the smaller specific gravity poorly corresponds to the content itself to make the measurement of the amount of this content unreliable.

If the requirement (2) is not met and c:d=1:less than 1, the lower edge of the central hole of the pressure plate is pressed against the airtightly sealed flexible container with an acute angle to consequently cause the airtightly sealed flexible container to become wrinkled and/or damaged. On the other hand, if the requirement (2) is not met and c:d=1:greater than 3, the central hole is too small at the upper surface of the pressure plate to produce a reasonably large projected image of the surface of the content with the smaller specific gravity. In either case, the measurement of the amount of the content becomes unreliable.

If the requirement (3) is not met and t is smaller than 0.5T, the area where the pressure plate is pressed against the airtightly sealed flexible container is too small and excessively high pressure can be applied to the-container so that the latter may be wrinkled and/or damaged. On the other hand, if the requirement (3) is not met and t is greater than 1T, the pressure plate may be too heavy and a larger and sophisticated machine may be required to handle such a large and heavy pressure plate if it may not provide any problem on the result of measurement.

According to the fifth aspect of the invention, by placing a sheet of translucent or opaque film in close contact with the surface of an object of examination the surface temperature distribution of the object of examination can be accurately determined regardless if the surface of the object carries thereon printed letters and/or decorative design members or not. Hence, such a method is particularly advantageous for determining the amount of the fluid content with a smaller specific gravity in airtightly sealed flexible containers containing contents with different specific gravities that are automatically separated from each other when held to a stationary state such as liquid and gas or water and oil by determining the surface temperature distribution of the airtightly sealed flexible container by means of electromagnetic waves.

Now, the present invention will be described further by referring to the accompanying drawings that illustrate preferred modes of realizing the invention.

DETAILED DESCRIPTION OF THE INVENTION

Figure 1:
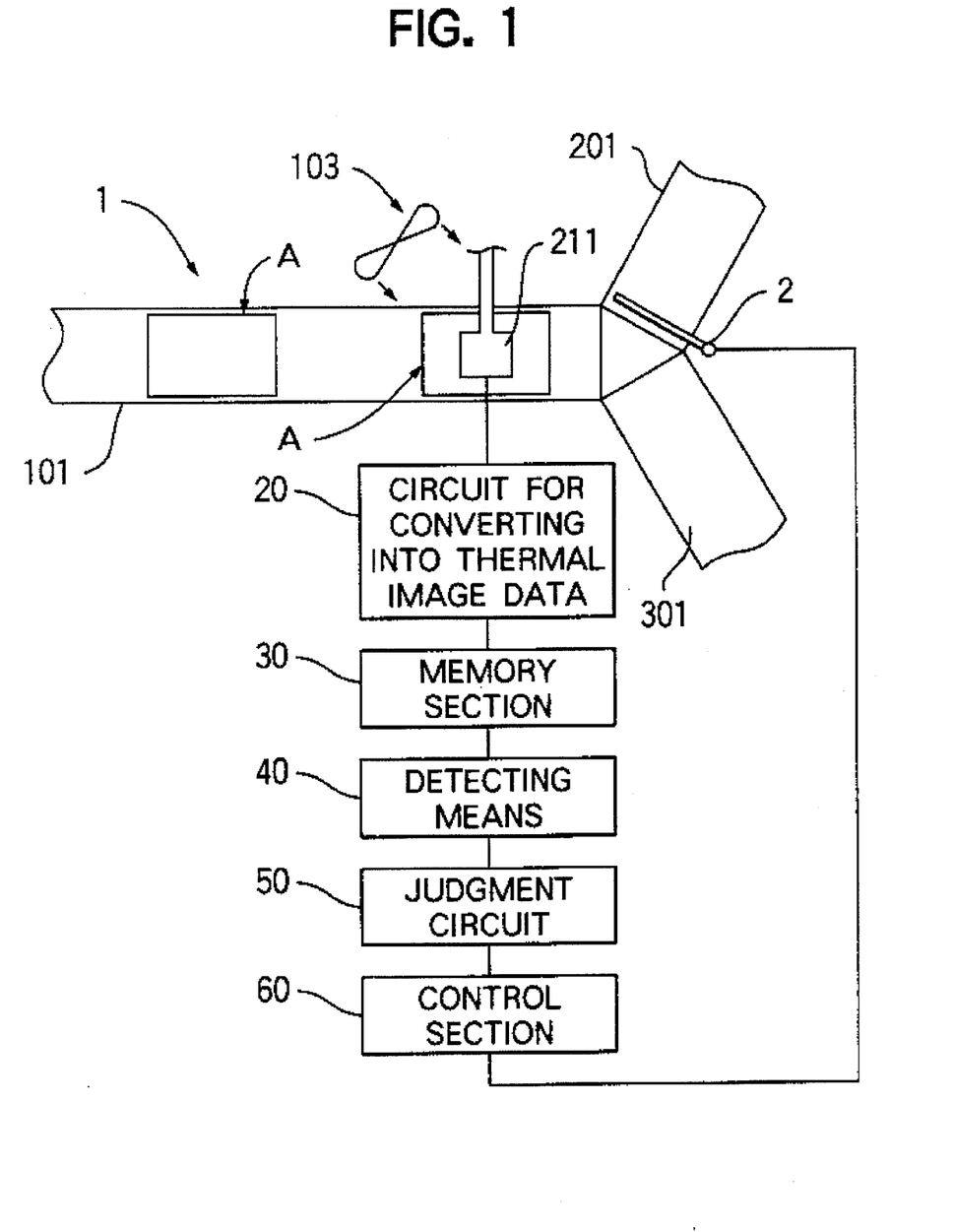
FIG. 1 is a schematic view of a measuring/sorting system to be used with a method according to the invention of determining the amount of the gas content of an airtightly sealed container containing gas.

FIG. 1 shows a schematic view of a measuring/sorting system to be used with a method according to the invention of determining the amount of a component content of an airtightly sealed container containing gas. Referring to FIG. 1, the system is generally denoted by reference numeral 1 and comprises a first conveyor (conveying path) 101 for conveying airtightly sealed containers containing gas A such as retort pouches containing contents with different specific gravities such as stew or soup having a greater specific gravity and air or inert gas having a smaller specific gravity in a flatly laid state. The conveyor is moved continuously or intermittently at a rate not exceeding 0.1 m/sec.

Figure 2:
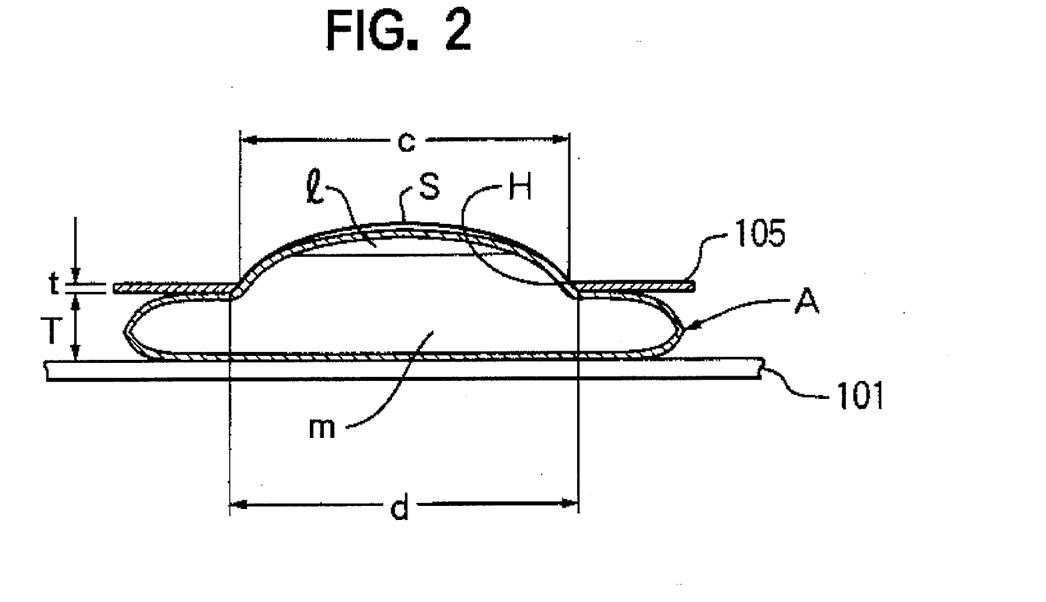
FIG. 2 is a schematic side view of an airtightly sealed container containing gas and a pressure plate showing how the pressure plate is pressed against the container for the purpose of the present invention.

A detector 211 which will be described in detail hereinafter is located above the first conveyor 101 to determine the area of a projected image of the gas content 1 of the container A. For determining the area of a projected image of the gas content of the container A, a pressure plate 105 provided with a central hole H is pressed against the airtightly sealed container A containing gas in a manner as shown in FIG. 2 so that the gas content 1 can keep a given profile. Reference symbol m in FIG. 2 denotes the substantive content of the container. A sheet S of thin film of silicon rubber, synthetic resin such as polysilicon or metal foil such as aluminum foil is placed between the airtightly sealed container A containing gas and the pressure plate 105. The sheet S has a thickness of 0.01 to 0.2 mm.

Figure 3:
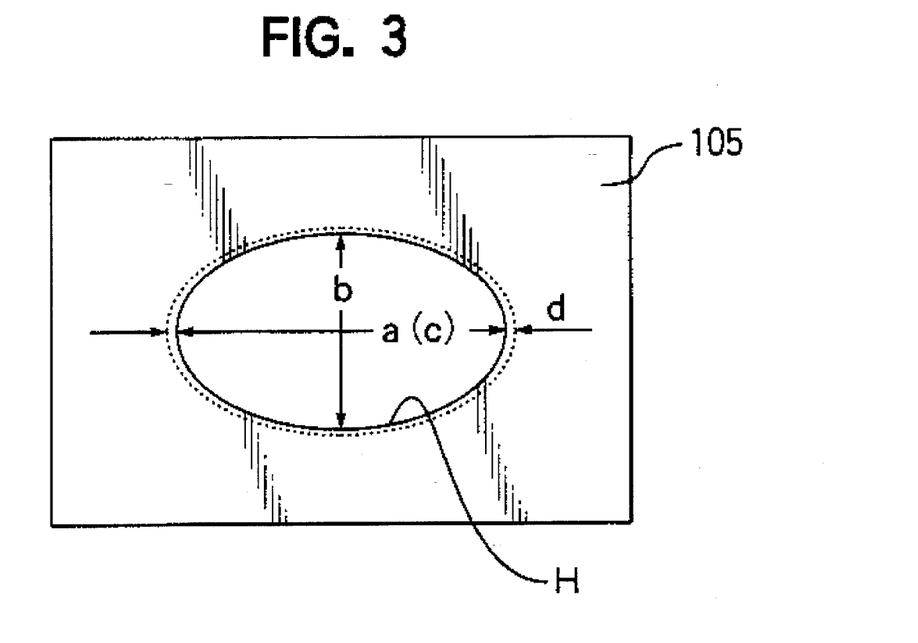
FIG. 3 is a schematic plan view of the pressure plate of FIG. 2.

The pressure plate 105 preferably has an outline similar to that of the airtightly sealed container A containing gas. As shown in FIG. 3, if the length of the longest axis of the central hole H of the pressure plate 105 is a and the maximum possible length of the, axis perpendicular to the longest axis of the central hole H is b, there is a relationship of b:a=1:1 to 2 between a and b. On the other hand, if the length of the longest axis of the central hole H on the upper surface of the pressure plate 105 is c and the length of the longest axis of the central hole H on the lower surface of the pressure plate 105 is d, c and d preferably shows a of c:d=1:1 to 3. Finally, if the height of the airtightly sealed container A containing gas is T and the thickness of the pressure plate 105 is 5, t and T preferably shows a relationship of $t=(0.05 \text{ to } 1)T$.

A second conveyor 201 for forwarding good airtightly sealed containers A containing gas to a next processing step such as a sterilization step and a third conveyor 301 for forwarding bad airtightly sealed containers A containing gas along a different route, are linked to the first conveyor 101 at the downstream end thereof. A rocking sorter 2 is provided near the junction of the first, second and third conveyors 101, 201 and 301 to sort out airtightly sealed containers A containing gas into good ones and bad ones depending on the detected gas content. The rocking sorter 2 can selectively link the first conveyor 101 to the second conveyor 201 or the third conveyor 301 by changing its rocking behavior to sort out airtightly sealed container A containing gas into good ones and bad ones depending on the detected gas content.

As shown in FIG. 1, a cooling air feeder 103 for supplying cooling air is provided upstream relative to the detector 211 along the first conveyor 101 to cool airtightly sealed containers A containing gas. The surface of each airtightly sealed container A containing gas normally shows a difference in the thermal capacity between areas held in contact with the gas content 1 (hereinafter referred to as gas contacting areas of the surface of the airtightly sealed container containing gas) and areas held in contact with the substantive content m (hereinafter referred to as substance contacting areas of the surface of the airtightly sealed container containing gas). When cooled with air supplied from the cooling air feeder 103, the gas contacting areas and the substance contacting areas of the surface of the airtightly sealed container containing gas produce a temperature difference therebetween so that they can be clearly identified from a projected image of the surface of the content.

The use of a cooling air feeder 103 is particularly effective when the substantive content is hot stew or soup that has just been prepared. The cooling air feeder 103 may be replaced by a cooling water feeder for cooling airtightly sealed containers containing gas with sprayed cold water or a cooling water pool for dipping airtightly sealed containers in cold water.

The cooling air feeder 103 may be replaced with a heating means. The use of a heating means is particularly effective when the substantive content is cold. A heating means that can be used for the purpose of the present invention may be a hot air feeder for blowing hot air to airtightly sealed containers containing gas, a hot water feeder for heating airtightly sealed containers with sprayed hot water or a hot air pool for dipping airtightly sealed containers in hot water.

As shown in FIG. 1, a detector 211 is arranged above the first conveyor 101 at a position downstream to the cooling air feeder 103 in order to detect the temperature distribution of the surface of the airtightly sealed container A containing gas by means of infrared rays irradiated from the surface of the container A. The detector 211 comprises a circuit 20 for converting obtained temperature data into thermal image data, a memory section 30 for storing thermal image data, an area determining means 40 for determining by calculation the total area that is found within a predetermined temperature range from the obtained thermal image data and a judgment circuit 50 for determining if the total area detected by the area detecting means 40 is found within a predetermined range or not and a control section 60 for controlling the operation of the rocking sorter 2 according to the output of the judgment circuit 50.

The detector 211 may be so designed as to detect the temperature distribution of the entire surface of the airtightly sealed container A containing gas or the temperature of a single spot or a plurality of spots on the surface of the airtightly sealed container A containing gas.

Now, the operation of the measuring/sorting system 1 for airtightly sealed containers containing gas will be described. The measuring/sorting system 1 has a configuration as described above and moves airtightly sealed containers A containing gas on a continuous basis by means of the first conveyor 101. As each airtightly sealed container A containing gas gets to the cooling air feeder 103, the former is cooled by the latter to produce a conspicuous temperature difference between the gas contacting areas and the substance contacting areas of the surface of the airtightly sealed container containing gas. For the purpose of the present invention, cooling air is typically required to be within a temperature range of $-30°$ to $+30°$ C.

Simultaneously with or immediately after the cooling operation, the detector 211 detects areas within a predetermined temperature range on the surface of the airtightly sealed container A containing gas by means of infrared rays irradiated from the airtightly sealed container A containing gas. The obtained temperature data are converted into thermal image data by the circuit 20 for converting temperature data in to thermal image data and stored in the memory section 30.

Subsequently, the area detecting means 40 determines by calculation the total area that are found within a predetermined temperature range on the surface of the airtightly sealed container containing gas or the sum of the projected gas contacting areas of the surface of the airtightly sealed container containing gas. Specifically speaking, the predetermined temperature range as cited above is between 30° and 50° C. when the temperature of the substantive content is 70° C. Thereafter, the judgment circuit 50 determines if the sum of the detected gas contacting areas is found within a predetermined range or not.

It should be noted that the gas contacting areas of the surface of an airtightly sealed container A containing gas is a function of the volume of the gas contained in the airtightly sealed container A and the ratio of the volume of the gas to the overall volume of the container. Therefore, it can easily be determined if the volume of the gas in an airtightly sealed container is within a predetermined appropriate range or not by determining the gas contacting areas of the surface of the airtightly sealed container containing gas. The relationship between the sum of the projected gas contacting areas of the surface of an airtightly sealed container containing gas and the volume of the gas in the airtightly sealed container can be strictly defined without difficulty by using different volumes of gas in the airtightly sealed container and collecting data on the sum of the gas contacting areas of the surface of the airtightly sealed container corresponding to each selected volume of gas.

With the above described determination process, if the sum of the gas contacting areas of the surface of an airtightly sealed container A containing gas is found within a predetermined range, the container is judged to be a good one. On the other hand, if the sum of the gas contacting areas of the surface is not found within the predetermined range, the container is judged to be a bad one containing too much or too little gas.

Then, the control section 60 controls the operation of the rocking sorter 2 from the time when the thermal profile of the surface of an airtightly sealed container A containing gas determined by the detector 211 at the time when the container arrives to the downstream end of the first conveyor 101 on the basis of the judgment of the judgment circuit 50. The rocking sorter 2 links the first conveyor 101 either to the second conveyor 201 or to the third conveyor 301 according to the control signal transmitted from the control section 60 so that the airtightly sealed container A containing gas is forwarded to the second conveyor 201 if iS a good one and to the third conveyor 301 if it is a bad one.

Figure 4:
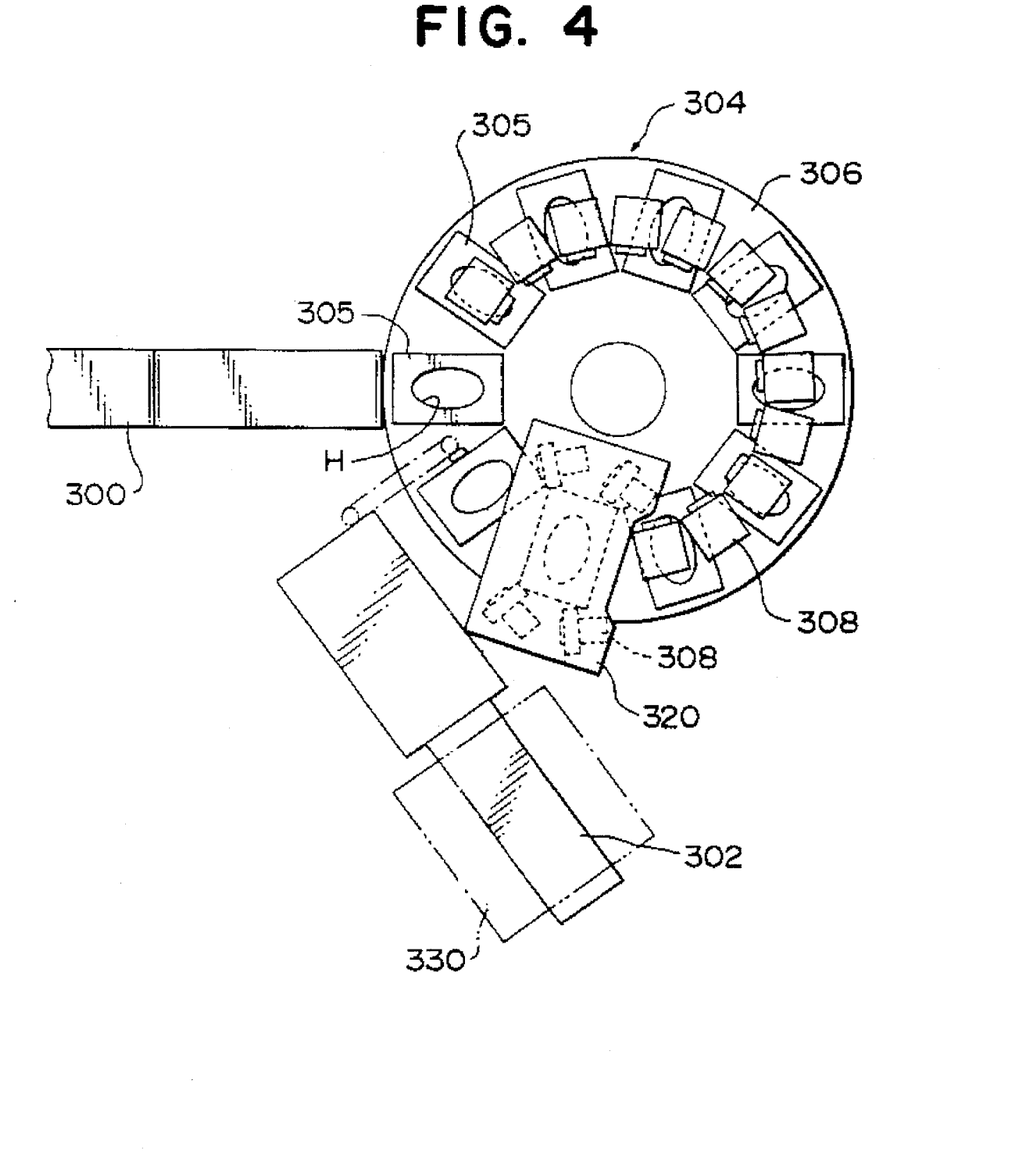
FIG. 4 is a schematic plan view of another measuring/sorting system to be used with a method according to the invention of determining the amount of the gas content of an airtightly sealed flexible container containing gas.
Figure 5:
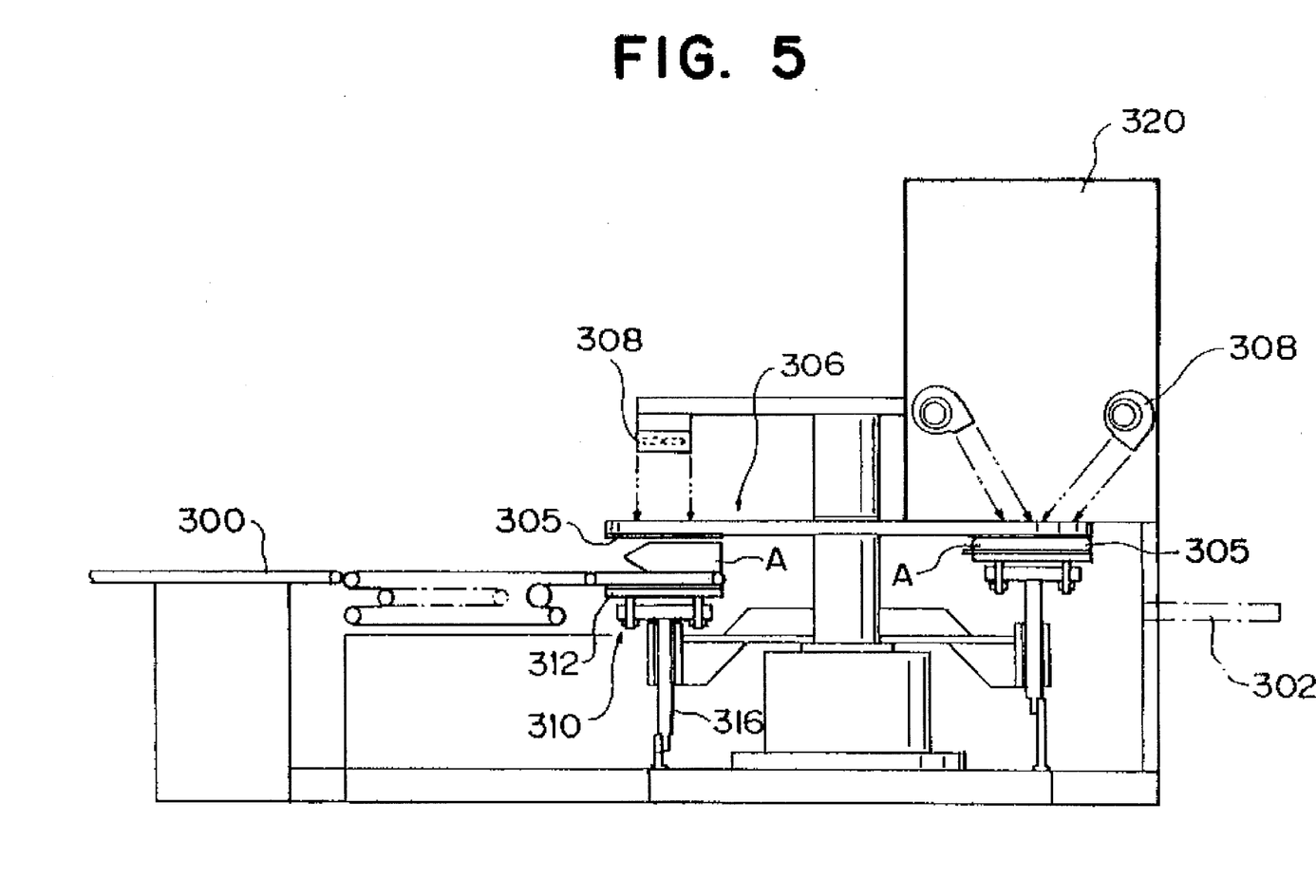
FIG. 5 is a schematic sectional side view of the system of FIG. 4.

FIG. 4 shows a schematic plan view of another measuring/sorting system to be used with a method according to the invention of determining the amount of the gas content of an airtightly sealed flexible container containing gas and FIG. 5 shows a schematic sectional side view of the system of FIG. 4. Referring now to FIGS. 4 and 5, the system comprises a first linear conveyor 300, a second linear conveyor 302 and a measuring/sorting unit 304 disposed close to the downstream end of the first conveyor 300 and the upstream end of the second conveyor 302.

The measuring/sorting unit 304 has a circular conveying path 306 for intermittently moving airtightly sealed containers A containing gas and a plurality of pairs of cooling fans 308 (only twelve fans are shown in FIG. 4) arranged above the conveying path 306 for blowing cooling air from above onto airtightly sealed containers A containing gas moving on the conveying path 306. The conveying path 306 comprises a plurality of continuously disposed conveying members 310 and pressure plates 305, each having a central hole H, are securely held above the respective conveying members 310. Receiving tables 312 are arranged below the conveying members 310 and can be vertically displaced by means of respective cylinders 316. A detector 320 having a configuration the same as that of the detector 211 of the first measuring/sorting system is arranged above the downstream end of the circular conveying path 306. The second linear conveyor 302 is provided with a weighing apparatus 330 for weighing the total weight of each airtightly sealed container A containing gas and a sorter (not shown) for sorting out good airtightly sealed containers A containing gas from no good containers.

For operating the second measuring/sorting system, each airtightly sealed container A containing gas brought in on the first linear conveyor 300 is moved onto one of the conveying members 310 of the conveying path 306. The airtightly sealed containers A containing gas carried by the respective conveying members 310 are continuously cooled from above by the cooling fans 308. Meanwhile, the airtightly sealed containers A containing gas and carried by the respective conveying members 310 are raised by the respective receiving table 312 as the respective cylinders 316 are extended upwardly until they are pressed against the respective pressure plates 305. The airtightly sealed container A containing gas moved to the downstream end of the circular conveying path 306 under this condition is then detected by the detector 320 for a projected image of the gas contacting areas of the surface of the container. Thereafter, the airtightly sealed container A containing gas is moved out of the circular conveying path 306 and onto the second linear conveyor 302. On the second linear conveyor 302, the airtightly sealed container A containing gas is weighed by the weighing apparatus 330 and then the ratio of the gas content to the substantive content of the container is determined by calculation from the data obtained by the detector 320 and the weighing apparatus 330. The sorter (not shown) is then operated to sort out good airtightly sealed containers A containing gas from bad ones according to control signals generated from calculated values of gas content ratio for the respective containers.

In an alternative measuring/sorting system that can be used for the purpose of the present invention, the detector may be arranged downstream relative to the cooling air feeder so that cooling air may not be blown onto the airtightly sealed container A containing gas at or near the detector. In still another alternative measuring/sorting system, the judgment circuit may be so designed that it determines if the gas content of an airtightly sealed container A containing gas is found within a predetermined range or not by using the result of calculation of a calculating circuit for calculating the volume of the gas content from the area detected by a detecting means instead of directly determining from the projected gas contacting areas of the surface detected by a detecting means.

Neither a cooling means nor a heating means is provided in still another alternative measuring/sorting system that can be used for the purpose of the present invention as such a system is used for airtightly sealed containers containing a substantive content having a temperature that differs significantly from room temperature. If such is the case, the temperature difference between the gas contacting areas and the substance contacting areas of the surface of an airtightly sealed container A becomes apparent after a certain period of time so that the ratio of the gas content to the substantive content can be determined by a thermal infrared detector.

What is claimed is:

1. A method of determining the amount of the fluid content with a smaller specific gravity in an airtightly sealed flexible container containing first and second contents with different specific gravities that are mutually immiscible with respect to each other, wherein the amount of the content is determined by externally applying pressure to the airtightly sealed flexible container to increase the inner pressure thereof and collecting data on the stratified layers of the fluid content with the smaller specific gravity, wherein the external pressure is applied by pressing a pressure plate having a hole through the plane of its surface against a part of an upper surface of the container from a vertical direction above the container.

2. A method of determining the amount of the fluid content with a smaller specific gravity in an airtightly sealed flexible container according to claim 1, wherein the amount of the content is determined by forming a projected image of the fluid content with the smaller specific gravity and calculating the volume of the content from the area of the projected image.

3. A method of determining the amount of the fluid content with a smaller specific gravity in an airtightly sealed flexible container according to claim 1, wherein the area of a projected image of the content with the smaller specific gravity is determined by processing a photographically taken image of the content.

4. A method of determining the amount of the fluid content with a smaller specific gravity in an airtightly sealed flexible container according to claim 1, wherein the area of the projected image of the content with the smaller specific gravity is determined by an image of the content which is formed with a fluoroscopy system.

5. A method of determining the amount of the fluid content with a smaller specific gravity in an airtightly sealed flexible container according to claim 1, wherein the area of the projected image of the content with the smaller specific gravity is determined by means of an image of the content obtained by irradiating the container with infrared rays to produce temperature distribution data of the container and processing the obtained temperature distribution data.

6. A method of determining the amount of the fluid content with a smaller specific gravity in an airtightly sealed flexible container according to claim 1, wherein the amount of the content is determined by collecting data on the surface area of the content with the smaller specific gravity.

7. A method of determining the amount of the fluid content with a smaller specific gravity in an airtightly sealed flexible container according to claim 1, wherein the amount of the content is determined by collecting data on the outer periphery of the content with the smaller specific gravity.

8. A method of determining the amount of the fluid content with a smaller specific gravity in an airtightly sealed flexible container containing first and second contents with different specific gravities that are mutually immiscible with respect to each other, wherein the amount of the content is determined by externally applying pressure to the airtightly sealed flexible container to increase the inner pressure thereof and collecting data on a projected image of the surface of the content with the smaller specific gravity in the airtightly sealed flexible container while intermittently moving the airtightly sealed flexible container with a maximum moving speed not exceeding 0.1 m/sec.

9. A method of determining the amount of the fluid content with a smaller specific gravity in an airtightly sealed flexible container containing first and second contents with different specific gravities that are mutually immiscible with respect to each other, wherein the amount of the content is determined by externally applying pressure to the airtightly sealed flexible container to increase the inner pressure thereof and collecting data on a projected image of the surface of the content with the smaller specific gravity in the airtightly sealed flexible container with a maximum moving speed not exceeding 0. 1 m/sec.

10. A method of determining on a continuous basis the amount of the fluid content with a smaller specific gravity in an airtightly sealed flexible container according to claim 8, wherein the airtightly sealed flexible container is moved horizontally, vertically or obliquely.

11. A method of determining on a continuous basis the amount of the fluid content with a smaller specific gravity in an airtightly sealed flexible container according to claim 8, wherein the airtightly sealed flexible container is moved along a horizontal circle.

12. A pressure plate to be used for measuring the amount of the fluid content with a smaller specific gravity in airtightly sealed flexible containers containing first and second contents with different specific gravities that are mutually immiscible with respect to each other from a projected image of the surface of the airtightly sealed flexible container, wherein the pressure plate is provided with a central hole that satisfies the requirements of (1) b:a=1:1 to 2, where a is the length of the longest axis of the central hole of the pressure plate and b is the maximum possible length of the axis perpendicular to the longest axis of the central hole, and (2) c:d=1:1 to 3, where c is the length of the longest axis of the central hole on the upper surface of the pressure plate and d is the length of the longest axis of the central hole on the lower surface of the pressure plate.

13. A pressure plate to be used for measuring the amount of the fluid content with a smaller specific gravity in airtightly sealed flexible containers according to claim 12, wherein the pressure plate satisfies the requirement of t=0.05 to 1T, where T is the height of the flexible container and t is the thickness of the pressure plate.

14. A method of measuring the surface temperature distribution of an object of examination by means of electromagnetic waves irradiated from the surface, wherein the surface temperature distribution of the object of examination is measured by placing a sheet of translucent or opaque film in close contact with the surface of the object of examination.

15. A method of measuring the surface temperature distribution of an object of examination according to claim 14, wherein the object of examination is contained in an airtightly sealed flexible container.

16. A method of measuring the surface temperature distribution of an object of examination according to claim 14, wherein the surface of the airtightly sealed flexible container is pressed by a pressure plate having a central hole through the plane of its surface against a part of an upper surface of the container from a vertical direction above the container, and the central hole is covered by bonding a sheet of translucent or opaque film to the pressure plate.

* * * * *